(12) United States Patent
Lima et al.

(10) Patent No.: US 11,085,426 B2
(45) Date of Patent: Aug. 10, 2021

(54) ARTIFICIAL MUSCLE ACTUATORS

(71) Applicant: Lintec of America, Inc., Richardson, TX (US)

(72) Inventors: Marcio Dias Lima, Richardson, TX (US); Yang Yang, Richardson, TX (US); Luis Plata, Richardson, TX (US); Marilu Guerrero, Richardson, TX (US); Franklin Le, Richardson, TX (US); Randy Allen, Richardson, TX (US)

(73) Assignee: LINTEC OF AMERICA, INC., Richardson, TX (US)

( * ) Notice: Subject to any disclaimer, the term of this patent is extended or adjusted under 35 U.S.C. 154(b) by 0 days.

(21) Appl. No.: 16/466,131

(22) PCT Filed: Dec. 7, 2017

(86) PCT No.: PCT/US2017/065151
§ 371 (c)(1),
(2) Date: Jun. 3, 2019

(87) PCT Pub. No.: WO2018/106941
PCT Pub. Date: Jun. 14, 2018

(65) Prior Publication Data
US 2020/0063720 A1   Feb. 27, 2020

Related U.S. Application Data

(60) Provisional application No. 62/462,544, filed on Feb. 23, 2017, provisional application No. 62/431,717, filed on Dec. 8, 2016.

(51) Int. Cl.
*F03G 7/06* (2006.01)
*F16K 31/44* (2006.01)
(Continued)

(52) U.S. Cl.
CPC ............ *F03G 7/06* (2013.01); *F16K 31/44* (2013.01); *H01H 85/04* (2013.01);
(Continued)

(58) Field of Classification Search
CPC  F03G 7/06; F03G 7/065; H01H 85/04; F16K 31/44; H02N 11/006; A61F 2002/5066; H01B 1/18
See application file for complete search history.

(56) References Cited

U.S. PATENT DOCUMENTS 3,810,062 A   5/1974  Kozacka
3,969,695 A   7/1976  Belcher
(Continued)

FOREIGN PATENT DOCUMENTS

CN           101958394         11/2011
DE    10 2006 029 693 A1       3/2007
(Continued)

OTHER PUBLICATIONS

A Treatise On Highly Twisted Artificial Muscle: Thermally Driven Shape Memory Alloy and Coiled Nylon Actuators (Year: 2015).*
(Continued)

*Primary Examiner* — Audrey K Bradley
*Assistant Examiner* — Edward Bushard
(74) *Attorney, Agent, or Firm* — Greenblum & Bernstein, P.L.C.

(57) ABSTRACT

An actuator includes a plurality of artificial muscle fibers and at least one conducting material. The at least one conducting material electrically stimulates the plurality of artificial muscle fibers during activation of the actuator. An actuator device includes at least one artificial muscle fiber and at least one high-strength creep-resistant fiber.

5 Claims, 6 Drawing Sheets

(51) Int. Cl.
*H02N 11/00* (2006.01)
*H01H 85/04* (2006.01)
*H01B 1/18* (2006.01)
*A61F 2/50* (2006.01)

(52) U.S. Cl.
CPC .... *H02N 11/006* (2013.01); *A61F 2002/5066* (2013.01); *F03G 7/065* (2013.01); *H01B 1/18* (2013.01)

(56) References Cited

U.S. PATENT DOCUMENTS

| | | | |
|---|---|---|---|
| 5,229,739 | A | 7/1993 | Oh et al. |
| 5,963,121 | A | 10/1999 | Stygar et al. |
| 7,692,361 | B2 | 4/2010 | Kato |
| 8,076,829 | B2 | 12/2011 | Chen et al. |
| 8,633,795 | B2 | 1/2014 | Knab et al. |
| 9,425,010 | B2 | 8/2016 | Hentschel |
| 9,863,406 | B2 | 1/2018 | Li et al. |
| 2002/0113684 | A1 | 8/2002 | Arikawa et al. |
| 2004/0104801 | A1 | 6/2004 | Jollenbeck et al. |
| 2006/0125596 | A1 | 6/2006 | Darr et al. |
| 2006/0261709 | A1 | 11/2006 | Kato et al. |
| 2007/0132539 | A1 | 6/2007 | Richter et al. |
| 2010/0060406 | A1 | 3/2010 | Kim et al. |
| 2010/0234779 | A1 | 9/2010 | Asvadi et al. |
| 2011/0012476 | A1 | 1/2011 | Chen et al. |
| 2011/0279218 | A1 | 11/2011 | Salonga et al. |
| 2014/0132119 | A1 | 5/2014 | Whinnery et al. |
| 2014/0163664 | A1 | 6/2014 | Goldsmith |
| 2016/0025079 | A1 | 1/2016 | Li et al. |
| 2016/0340814 | A1* | 11/2016 | Ridley ............... B32B 15/04 |

FOREIGN PATENT DOCUMENTS

| | | |
|---|---|---|
| EP | 1 693 950 A1 | 8/2006 |
| JP | 56-130054 A | 10/1981 |
| JP | 60-77264 U | 5/1985 |
| JP | 11-215793 A | 8/1999 |
| JP | 2005-110494 A | 4/2005 |
| JP | 2005-176428 A | 6/2005 |
| JP | 2006-325335 A | 11/2006 |
| JP | 2007159222 A | 6/2007 |
| JP | 2007-300714 A | 11/2007 |
| JP | 2008-100901 A | 5/2008 |
| JP | 2009-32773 A | 2/2009 |
| JP | 2010-500895 A | 1/2010 |
| JP | 2011-125092 A | 6/2011 |
| JP | 2011-152031 A | 8/2011 |
| JP | 2012-530572 A | 12/2012 |
| JP | 2016-199900 A | 12/2016 |
| KR | 101 563 105 B1 | 10/2015 |
| KR | 20160117658 A | 10/2016 |
| TW | I553921 | 10/2016 |
| WO | 2005/027333 A1 | 3/2005 |
| WO | 2011/070912 A1 | 6/2011 |
| WO | 2014/022667 | 2/2014 |
| WO | 2015/196057 | 12/2015 |

OTHER PUBLICATIONS

Taiwanese Official Letter issued in Corresponding Taiwanese Patent Application No. 106143209 dated Feb. 10, 2020 (4 pages).
Office Action issued in corresponding U.S. Appl. No. 16/467,830 dated May 8, 2020 (13 pages).
International Search Report issued in PCT/US2017/065151 dated May 14, 2018 (6 pages).
Written Opinion issued in PCT/US2017/065151 dated May 14, 2018 (8 pages).
ACESElectromaterials: "Artificial muscles"; XP054978158; Aug. 4, 2015 (Aug. 4, 2015); retrieved from YouTube [online]: URL:https://www.youtube.com/watch?v=vVhUBENOqhg Time frame: 1:21-1:37.
International Search Report issued in PCT/US2017/065127 dated May 14, 2018 (5 pages).
Written Opinion issued in PCT/US2017/065127 dated May 14, 2018 (9 pages).
International Preliminary Report on Patentability issued in Application No. PCT/US2017/065150, dated Jun. 20, 2019 (11 pages).
International Preliminary Report on Patentability issued in Application No. PCT/US2017/065127, dated Jun. 20, 2019 (10 pages).
International Preliminary Report on Patentability issued in Application No. PCT/US2017/065151, dated Jun. 20, 2019 (9 pages).
International Search Report issued in PCT/US2017/065150 dated May 14, 2018 (5 pages).
Written Opinion issued in International Application No. PCT/US2017/065150 dated May 14, 2018 (10 pages).
Japan Official Action (Notice of Reasons for Rejection) issued in JP 2019-522498, dated Aug. 11, 2020, and English language translation thereof.
U.S. Appl. No. 16/467,830 to Marcio Dias Lima et al., filed Jun. 7, 2019.
U.S. Appl. No. 16/466,532 to Marcio Dias Lima et al., filed Jun. 4, 2019.
Japan Notice of Reasons for Rejection in JP Appl. No. 2019-530463, dated Sep. 7, 2020 and English translation.
Japan Notice of Reasons for Rejection in JP Appl. No. 2019-524041, dated Sep. 7, 2020 and English translation.
Japanese Official Action received in JP Application No. 2019-524041 dated Mar. 1, 2021, and English language translation thereof.
Taiwan Official Action and appended Search Report received in TW Patent Application No. 106143208, dated Jun. 22, 2021 and Computer Generated English language translation thereof.
Taiwan Official Action and appended Search Report received in TW Patent Application No. 106143209, dated Jun. 25, 2021 and Computer Generated English language translation thereof.
Notice of Reasons for Rejection received in JP 2019-530463, dated Jun. 14, 2021 and English language translation thereof.
European Office Action recited in European Patent Application No. 17 828 806.4, dated Jun. 25, 2021.

* cited by examiner

ARTIFICIAL MUSCLE ACTUATORS

CROSS-REFERENCE TO RELATED APPLICATIONS

This Application claims priority, pursuant to 35 U.S.C. § 119(e) to U.S. Provisional Application 62/431,717 filed on Dec. 8, 2016, and U.S. Provisional Application 62/462,544 file on Feb. 23, 2017, and which are incorporated by reference in their entireties.

BACKGROUND OF INVENTION

Thermally driven torsional actuators based on twisted polymeric and carbon nanotube (CNT) fibers and yarns have a wide range of applications. Artificial muscle actuators comprising twisted and/or coiled polymers have the advantage of low cost, high production volume, and design simplicity. Artificial muscle actuators may have advantages over small motors because of the greatly simplified engineering and lower product costs.

SUMMARY

In one aspect, an actuator device in accordance with the present disclosure may include a plurality of artificial muscle fibers and at least one conducting material that electrically stimulates the plurality of artificial muscle fibers during actuation.

In another aspect, an actuator device in accordance with the present disclosure may include at least one artificial muscle fiber and at least one high-strength creep-resistant fiber.

Other aspects and advantages of the claimed subject matter will be apparent from the following description and the appended claims.

BRIEF DESCRIPTION OF DRAWINGS

Certain embodiments of the disclosure will hereafter be described with reference to the accompanying drawings, where like reference numerals denote like elements. It should be understood, however, that the accompanying figures illustrate various implementations described herein and are not meant to limit the scope of various technologies described herein.

DETAILED DESCRIPTION

Figure 1:
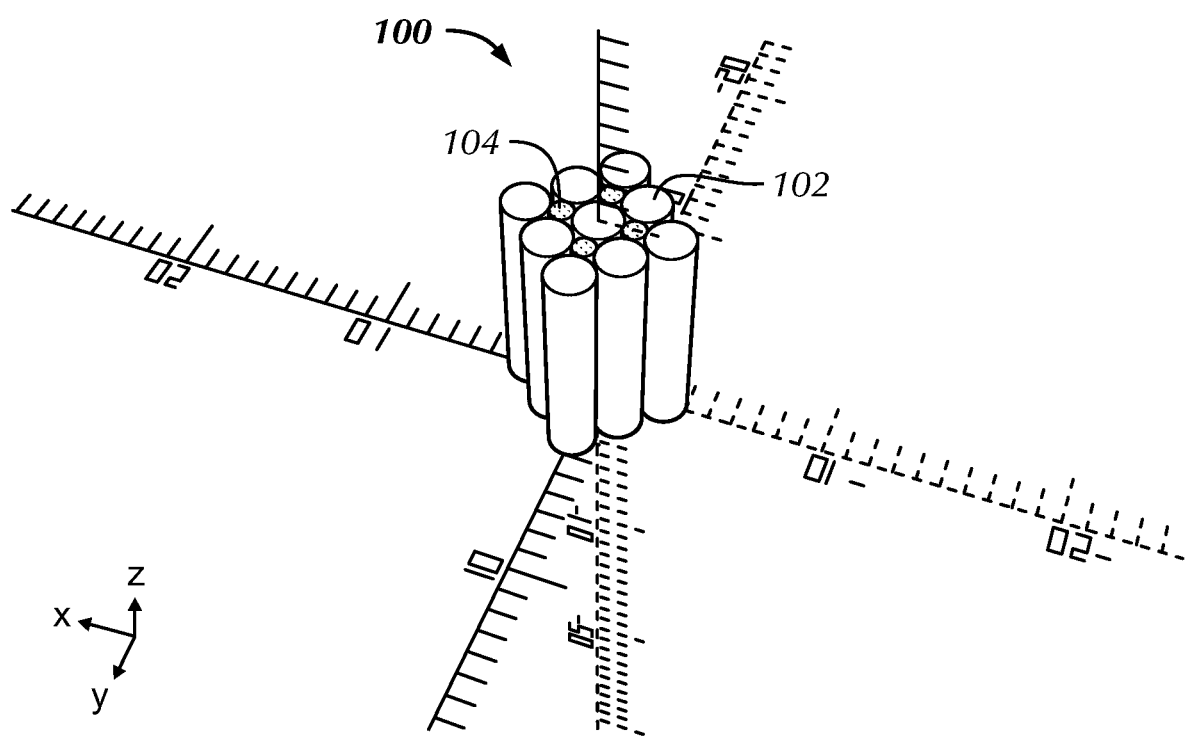
FIG. 1 is a schematic of an artificial muscle actuator bundle in accordance with one or more embodiments disclosed herein.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Embodiments of the present disclosure will now be described in detail with reference to the accompanying figures. Like elements in the various figures may be denoted by like reference numerals for consistency. Further, it will be apparent to one of ordinary skill in the art that the embodiments disclosed herein may be practiced without the specific details provided to allow a more thorough understanding of the claimed subject matter. Further still, one of ordinary skill in the art will readily recognize that the scale of the elements in the accompanying figures may vary without departing from the scope of the present disclosure.

One or more embodiments of the present disclosure relate to artificial muscle actuators. One or more embodiments include bundling of artificial muscle fibers to form an artificial muscle actuator. One or more embodiments include creep resistance. One of ordinary skill in the art will appreciate that the embodiments disclosed herein may be used in combination with other embodiments, or incorporated into other existing actuator technologies, such as those incorporated by reference above.

The term "or" is understood to be an "inclusive or" unless explicitly stated otherwise. Under the definition of "inclusive or," the expression "A or B" is understood to mean "A alone, B alone, or both A and B." Similarly, "A, B, or C" is understood to mean "A alone, B alone, C alone, both A and B, both A and C, both B and C, or A and B and C."

In accordance with embodiments disclosed herein, a carbon nanotube layer is comprised of a plurality of carbon nanotube (CNT) sheets stacked on top of each other. In one or more embodiments, the plurality of CNT sheets may comprise a single sheet wrapped over on itself multiple times. Such CNT sheets may be considered isotropic in accordance with embodiments disclosed herein. In one or more embodiments, these CNT sheets, when stacked on top of each other, become essentially inseparable and cannot be unwrapped. CNT layers in some cases may contain 50 CNT sheets, 100 CNT sheets, or more.

An artificial muscle device may also be referred to as a sheet muscle device, a hybrid nanofiber artificial muscle, a hybrid muscle device, a hybrid actuator, an artificial muscle actuator, or the like.

The term hybrid is used to indicate that CNT sheets are infiltrated with a guest actuation material to form one or more CNT layers, and further that the CNT layers may include other materials as well. For example, materials may include elastomers (e.g., silicone-based rubber, polyurethane, styrene-butadiene copolymer, natural rubber, and the like), fluorinated plastics (e.g., perfluoroalkoxy alkane (PFA), polytetrafluoroethylene (PTFE), fluorinated ethylene propylene (FEP), and the like), aramids, (e.g., Kevlar, nomex, and the like), epoxies, polyimides, paraffin wax, and the like.

In embodiments disclosed herein, a yarn is a long, continuous length of interlocked fibers. In a CNT yarn, the fibers are CNTs, and a core fiber is the fiber around which CNT layers are wrapped.

The term "or" is understood to be an "inclusive or" unless explicitly stated otherwise. Under the definition of "inclusive or," the expression "A or B" is understood to mean "A alone, B alone, or both A and B." Similarly, "A, B, or C" is understood to mean "A alone, B alone, C alone, both A and B, both A and C, both B and C, or A and B and C."

In general, embodiments of the invention relate to advancements in muscle fiber actuator technologies. For example, embodiments of the invention include an artificial muscle actuator that includes bundling of artificial muscle fibers. Embodiments of the invention also include creep resistance.

Embodiments of the invention include actuator materials, or artificial muscles, including twist-spun nanofiber yarn and twisted polymer fibers that generate torsional and/or tensile actuation when powered electrically, photonically, thermally, chemically, by absorption, or by other means. Embodiments of the invention include actuators that utilize coiled yarns or polymer fibers and may be either neat or include a guest.

In one or more embodiments, an artificial muscle actuator is comprised of bundled artificial muscle fibers. In accordance with embodiments disclosed herein, many small diameter fibers bound together may increase the total torque output compared to a single fiber of comparable total diameter. For example, as a consequence of yarn dynamics, the power output of a polymer muscle fiber may follow the relationship turns/length is inversely proportional to diameter. As such, an increased amount of twist may allow for the fiber to produce larger output for a given time period. Therefore, a bundle of muscle fibers may produce more torque than a single fiber of equal size.

As noted above, in one or more embodiments, the actuators may include a conducting material so that the actuation may be stimulated electrically. This conducting material may be incorporated into a bundle in a variety of ways. For example, the conducting material may take the form of one or more wires incorporated into the bundle of fibers as demonstrated in FIGS. 1-3.

FIG. 1 shows a schematic of an artificial muscle actuator bundle 100 in accordance with one or more embodiments disclosed herein. FIG. 1 includes nine artificial muscle fibers 102 and four conducting material wire structures 104. The conducting material wire structures 104 are formed in the gaps between the artificial muscle fibers 102, where the artificial muscle fibers 102 are arranged in a rectangular array.

Figure 2:
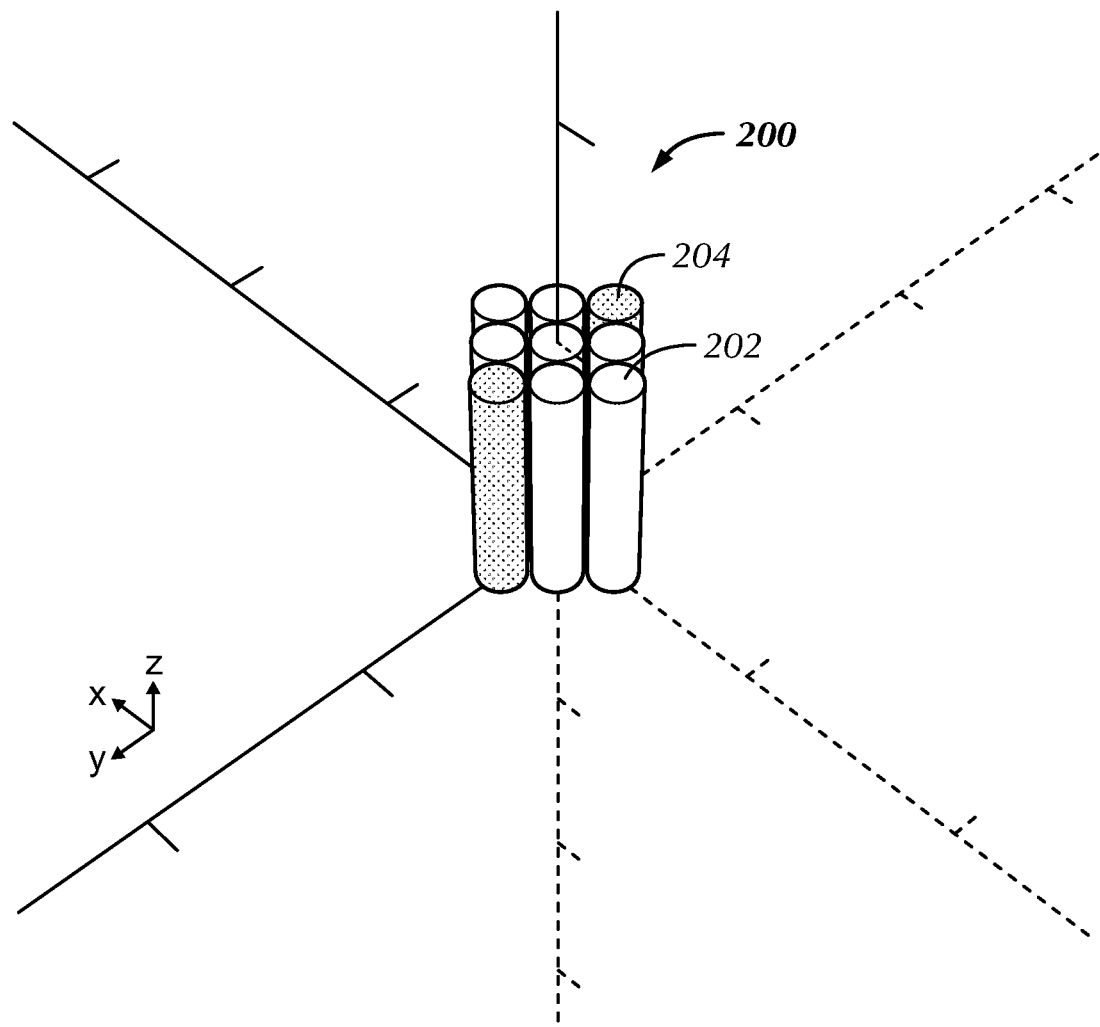
FIG. 2 is a schematic of a second artificial muscle actuator bundle in accordance with one or more embodiments disclosed herein.

FIG. 2 shows a schematic of an artificial muscle actuator bundle 200 in accordance with one or more embodiments disclosed herein. FIG. 2 demonstrates a configuration where the conducting material wire structures 204 and the artificial muscle fibers 202 are arranged in a rectangular array.

Figure 3:
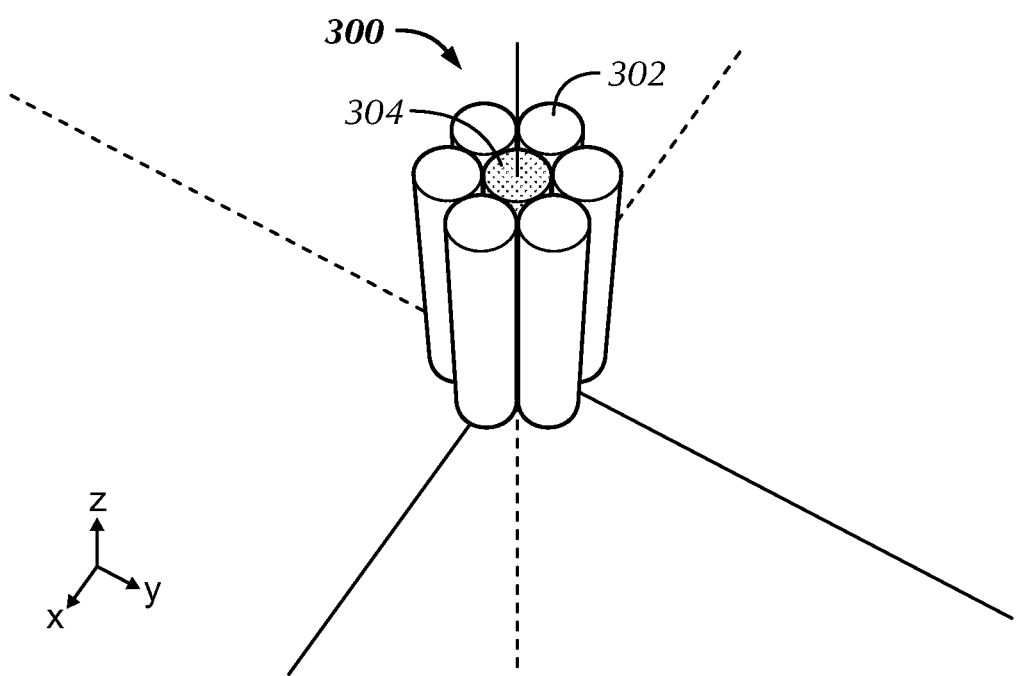
FIG. 3 is a schematic of a third artificial muscle actuator bundle in accordance with one or more embodiments disclosed herein.

Embodiments disclosed herein are not limited to rectangular arrays. FIG. 3 shows a schematic of an artificial muscle actuator bundle 300 in accordance with one or more embodiments disclosed herein. FIG. 3 demonstrates a configuration where a conducting material wire structure 304 and the artificial muscle fibers 302 are arranged in a hexagonal array.

One of ordinary skill in the art will appreciate that embodiments of the invention are not limited to just the configurations of FIGS. 1-3. The number of artificial muscle fibers and conducting structures, as well as the size of the artificial muscle fibers and conducting wire structures may be varied depending on the application.

Further, these embodiments are not limited to just wire-like structures for the conducting material as described above. In other words, the conducting material may take the form of any conducting material incorporated into the bundle. For example, the conducting material may also function as a binder to hold the fibers together.

In one or more embodiments, a conductive coating may be used for the conducting material in the bundle of artificial muscle actuators. The conductive coating may be coated around one or more of the artificial muscle fibers that make up the bundle of artificial muscle fibers. Further, the coating may encompass the entire fiber bundle in accordance with embodiments herein.

In one or more embodiments, the conducting material may be insulated from contact with other conducting materials present in the bundle. This may be especially useful for muscle bundles where the conductive pathway runs in a loop through the artificial muscle actuator. It may also be especially useful for designs where two electrically conductive muscle fibers are in contact with each other.

A wire may be placed in the center of the bundle of nanofibers, this wire may then increase the ease strain which may be placed onto the wire. It will also decrease manufacturing costs as the wire does not need to be wound around the individual fibers. The manufacturing process of winding the thin metal wire around the polymeric fibers has been the source of many quality assurance issues. An incomplete circuit due to the metal wire breaking will render that sample non-functional and it must be discarded.

The use of a single metal wire allows for only an apparatus which winds and coils the samples, and there is no need for winding a small wire or coating with a conductive layer. The bound artificial muscles are easier to produce on a large scale.

It is possible that with repeated twisting due to rotation the metal wire in the center of the bundle will fatigue and wear out. Thus, it may be especially preferable to use a more flexible material for the conductive joule heater. Carbon nanotube (CNT) yarns are especially preferred for this application because they do not fatigue easily and will greatly increase the lifespan of the artificial muscle.

The conductive pathway that breaks more often is the pathway between the artificial muscle fiber and ground, which is necessary for a bi-stable artificial muscle and for a muscle requiring different directions of angular rotation. This wire will undergo repeated flexing if, for example, attached to a device which rotates in an angular direction. A way to decrease the amount of stress on each segment of the wire must undergo can be done by increasing the length of the wire, but this can undesirably increase the dimensions of the final product. Once again a more flexible alternative is desired, and once again a CNT yarn represents an ideal option for providing this conductive path.

Another option, to avoid the need for a grounding wire to be attached to a device in the middle is to provide a conductive loop within the muscle fiber bundle itself. There may be two conductor insulate against contact with each other except at the end of the artificial muscle bundle opposite the power supply. In this way the current will pass through one conductor to the end of the muscle fiber and then return to the power supply by the other conductor which is parallel to the first conductor. If the conductors are composed of metal. They may simply have solder applied to the end of the device, to connect the two conductors electrically. This may further enable easy manufacturing. Further a metallized CNT yarn may have solder applied to it. Furthermore, this process may also be used where the conductor is a thin wire wrapped around some artificial muscles and where the artificial muscle fibers have a continuous conductive layer applied onto their surface. Other techniques for making an electrical connection may be used including a conductive paint, which may be particularly useful for embodiments highly absorbent CNT yarns serving as the conductor.

It is possible that the conductors are coated in an insulating layer to prevent electrical contact or they may be positioned opposite from each other in the artificial muscle fiber bundle, so that the non-conductive polymer muscle between them act to insulate each conductor from the other.

Friction plays a major role in how the bundle of muscles will operate. If the frictional force between each of the artificial muscle fibers in the bundle is too high, each artificial muscle fiber will not be able to operate independently of each other and will instead move as a single muscle fiber. If the friction generated between the muscle fibers is low enough, then the muscle fibers will be able to operate independently of each other. The advantage of bundling is that more torque can be produced from many small highly twisted muscle fibers bound together, than a single large highly twisted muscle fiber, where both the bundle and single artificial muscle fibers have the same total diameter. This perhaps surprising phenomenon is due to the relationship between the helix angle of the fiber and the number of twists that can be inserted per unit of length. $\tan(\alpha)=\pi TD$, where $\alpha$ is the helix angle of the yarn, T is the number of twists per meter, and D is the diameter of the fiber. The higher number of twists in an artificial muscle fiber segment the greater the torque output.

In order to prevent the electrical current passing through conductors to short circuit, it may be desirable to insulate the conductors from contact with each other. This may be especially useful for muscle bundles where the conductive pathway runs in a loop through the muscle. It may also be especially useful for designs where two electrically conductive muscle fibers come into contact with each other. It is difficult to adequately insulate a thin copper wire, but it can be done. It may also be useful to utilize Carbon Nanotubes as the conductive material of choice which may more easily be insulated. Another option is to use a conductive polymer or material for the artificial muscle fiber itself. This may still more easily have an insulating layer applied to it.

An artificial muscle fiber will suffer from creep over time and with repeated use, where creep is the loss of tension in the muscle due to deformation of the muscle fiber itself. Creep is a natural process that occurs over time and is dependent upon many factors, such as load, temperature, and crucially the properties of the fiber.

Nylon, a common artificial muscle material, has the advantages of low cost and manufacturability. Unfortunately, nylon is also susceptible to creep. One approach is to replace nylon with a polymer less susceptible to creep, or other high-strength material such as carbon nanotube yarns.

In one or more embodiments, creep may be reduced by removing some of the load on the muscle fiber and by applying a high-strength creep-resistant fiber. In one or more embodiments, a bundle of muscle fibers includes at least one high-strength creep-resistant fiber.

Figure 4:
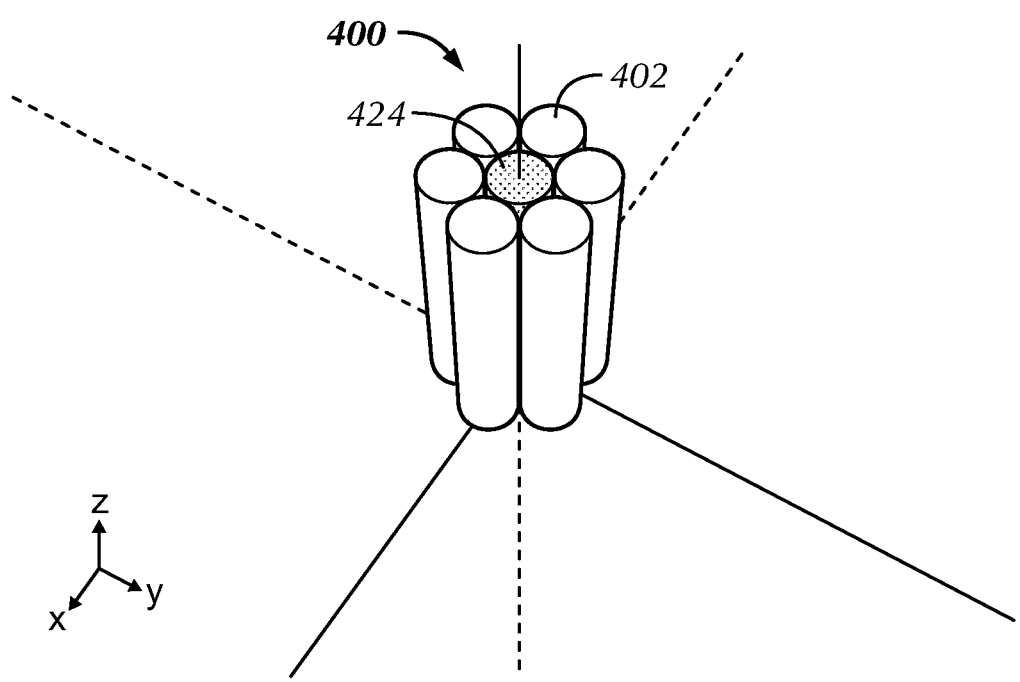
FIG. 4 is a schematic of an artificial muscle actuator bundle with creep resistance in accordance with one or more embodiments disclosed herein.

As seen in FIG. 4, in one or more embodiments, an artificial muscle actuator may comprise a bundle of artificial muscle fibers 402 arranged in a hexagonal array around a central high strength fiber 424.

Figure 5:
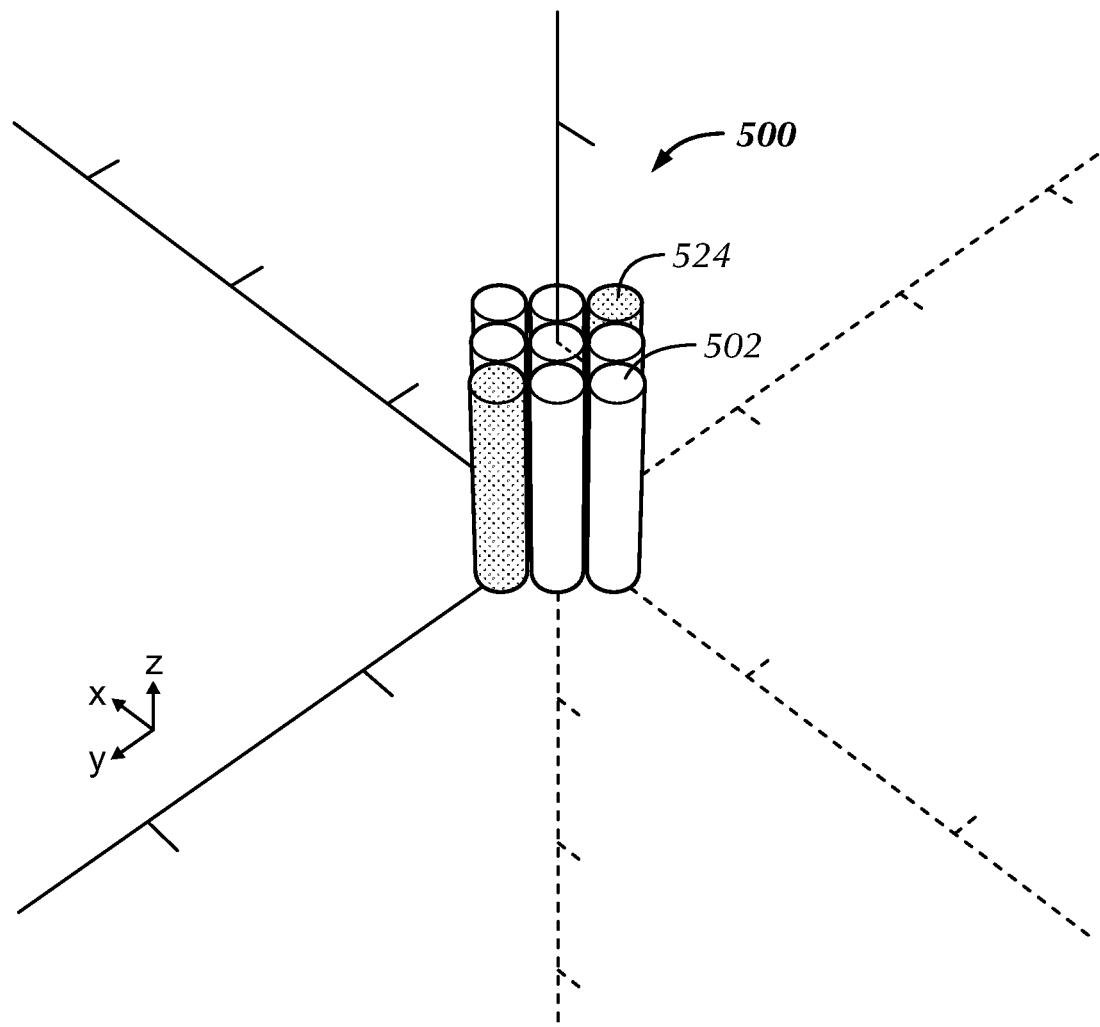
FIG. 5 is a schematic of a second artificial muscle actuator bundle with creep resistance in accordance with one or more embodiments disclosed herein.

As seen in FIG. 5, in one or more embodiments, an artificial muscle actuator 500 may comprise a bundle of artificial muscle fibers 502 arranged in a square array with a pair of high strength fibers 524 at opposite corners of the array.

For rotational artificial muscles there is no need to twist or coil the high-strength fiber, since the high-strength fiber does not need to actuate at all. Example high-strength fibers may include Kevlar™ and Vectran™. Carbon nanotube (CNT) yarns may be capable of simultaneously prevent creep and provide the ohmic heating necessary for electrical actuation of the muscle fibers. Untwisted nylon fiber has slightly greater resistance to creep than highly twisted nylon fiber, meaning that a combination of actuating (twisted) nylon fibers and non-actuating (untwisted) nylon fibers may be used together in a bundle. In one or more embodiments, a small diameter fiber may be used to minimize heat capacitance, since the entire bundle must be heated and cooled to produce actuation. Heating a fiber that does not produce actuation decreases the energy efficiency of the bundle and can increase cooling times, which negatively affects actuation rates. As shown in FIG. 4, artificial muscle fiber 402 is twisted about its central longitudinal axis. The high-strength creep-resistant fiber 424 has a central longitudinal axis and is untwisted. An outer periphery of the artificial muscle fiber 402 contacts an outer periphery of the high-strength creep-resistant fiber 424. The central longitudinal axis of the artificial muscle fiber 402 is spaced apart from and extends parallel to the central longitudinal axis of the high-strength creep-resistant fiber 424.

Figure 6:
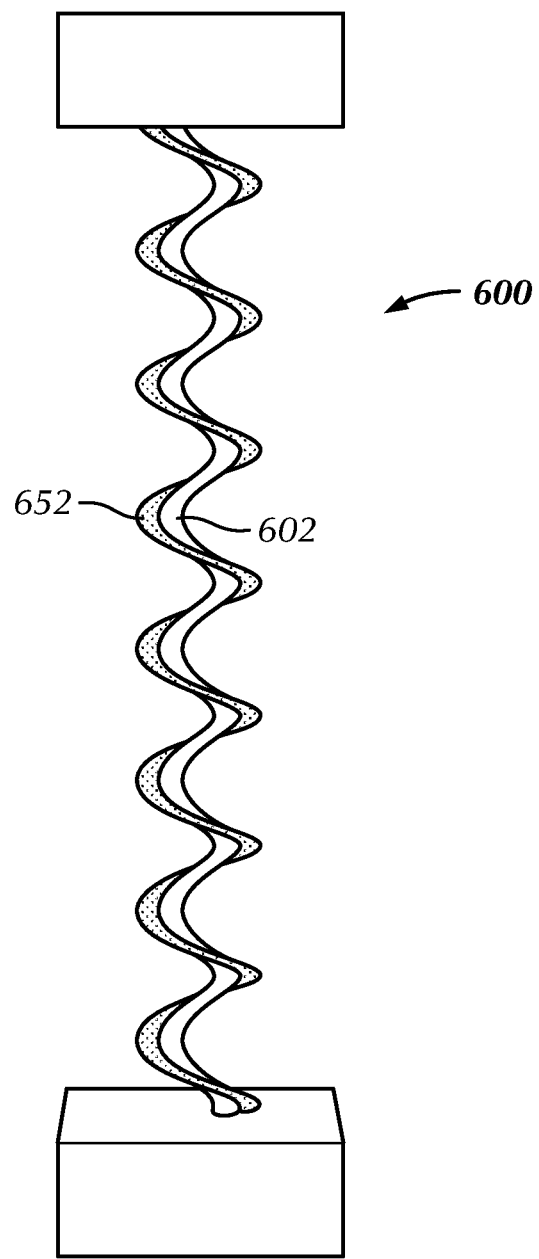
FIG. 6 is a schematic of coiled artificial muscle actuator running parallel to a spring in accordance with one or more embodiments disclosed herein.

Coiled linear-actuating muscles can also have a creep-resistant material working in tandem with the muscle. As shown in FIG. 6, in one or more embodiments, a spring 652 may be applied running parallel to the coiled artificial muscle 602. The spring 652 may wind around the artificial muscle fiber as shown in FIG. 3, or it may be juxtaposed to the artificial muscle (not shown), possibly in an array of fibers and springs (as shown in FIG. 7).

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An actuator device, comprising:
   at least one artificial muscle fiber having a central longitudinal axis, the at least one artificial muscle fiber being twisted about its central longitudinal axis; and
   at least one high-strength creep-resistant fiber having a central longitudinal axis, the at least one high-strength creep-resistant fiber being untwisted,
   wherein an outer periphery of the at least one artificial muscle fiber contacts an outer periphery of the at least one high-strength creep-resistant fiber, and
   wherein the central longitudinal axis of the at least one artificial muscle fiber is spaced apart from and extends parallel to the central longitudinal axis of the at least one high-strength creep-resistant fiber.

2. The actuator device according to claim 1, wherein the at least one artificial muscle fiber is a plurality of artificial muscle fibers that are bundled together in a hexagonal array with the at least one high-strength creep-resistant fiber at the center of the hexagonal array,
   wherein each of the plurality of artificial muscle fibers has a corresponding central longitudinal axis, each of the plurality of artificial muscle fibers being twisted about its corresponding central longitudinal axis, and
   wherein a corresponding outer peripheral surface of each of the plurality of artificial muscle fibers contacts the outer peripheral surface of the at least one high-strength creep-resistant fiber.

3. The actuator device according to claim 1, the at least one high-strength creep-resistant fiber comprising carbon nanotube yarn, the carbon nanotube yarn providing ohmic heating to the at least one artificial muscle fiber.

4. The actuator device according to claim 1, wherein the at least one high-strength creep-resistant fiber comprises untwisted nylon fiber.

5. The actuator device according to claim 4, wherein the at least one artificial muscle fiber comprises twisted nylon fibers.

* * * * *